US010925996B2

(12) United States Patent
Hoogenboom et al.

(10) Patent No.: US 10,925,996 B2
(45) Date of Patent: Feb. 23, 2021

(54) CROSS-LINKED POLYMERS AND IMPLANTS DERIVED FROM ELECTROPHILICALLY ACTIVATED POLYOXAZOLINE

(71) Applicant: GATT Technologies B.V., Nijmegen (NL)

(72) Inventors: Richard Hoogenboom, Terneuzen (NL); Johannes Caspar Mathias Elizabeth Bender, Utrecht (NL); Jan Cornelis Maria Van Hest, Nijmegen (NL)

(73) Assignee: GATT TECHNOLOGIES BV, Nijmegen (NL)

(*) Notice: Subject to any disclaimer, the term of this patent is extended or adjusted under 35 U.S.C. 154(b) by 79 days.

(21) Appl. No.: 16/378,245

(22) Filed: Apr. 8, 2019

(65) Prior Publication Data
US 2019/0231923 A1 Aug. 1, 2019

Related U.S. Application Data

(60) Division of application No. 15/617,009, filed on Jun. 8, 2017, now Pat. No. 10,314,936, which is a continuation of application No. 13/978,045, filed as application No. PCT/NL2012/050001 on Jan. 2, 2012, now Pat. No. 9,770,527.

(30) Foreign Application Priority Data

Jan. 4, 2011 (EP) ...................................... 1150099

(51) Int. Cl.
A61L 24/04 (2006.01)
A61L 24/06 (2006.01)
A61L 27/18 (2006.01)
A61L 31/06 (2006.01)
C08G 73/02 (2006.01)
C08J 3/24 (2006.01)
A61K 47/50 (2017.01)

(52) U.S. Cl.
CPC ............ A61L 24/046 (2013.01); A61K 47/50 (2017.08); A61L 24/06 (2013.01); A61L 27/18 (2013.01); A61L 31/06 (2013.01); C08G 73/0233 (2013.01); C08J 3/246 (2013.01); C08J 2300/10 (2013.01); C08J 2379/02 (2013.01)

(58) Field of Classification Search
None
See application file for complete search history.

(56) References Cited

U.S. PATENT DOCUMENTS 3,996,237 A    12/1976  Tomalia
5,614,587 A     3/1997  Rhee et al.
5,635,571 A     6/1997  Frechet et al.
5,874,500 A *   2/1999  Rhee .................... A61L 24/043
                                                        525/419
6,465,582 B1 * 10/2002  Higginbottom ...... C07D 263/14
                                                        428/402
6,566,406 B1    5/2003  Pathak et al.
9,416,228 B2    8/2016  Bender et al.
9,770,527 B2    9/2017  Hoogenboom et al.
10,314,936 B2 * 6/2019  Hoogenboom ......... A61L 31/06
2002/0042473 A1 4/2002  Trollsas et al.
2003/0119985 A1 6/2003  Sehl et al.
2004/0157157 A1 8/2004  Saito et al.
2005/0002893 A1 1/2005  Goldmann
2006/0258560 A1 11/2006 Yang et al.
2011/0123453 A1 5/2011  Bentley et al.
2011/0251574 A1 10/2011 Hedrich et al.
2012/0041481 A1 2/2012  Daniloff et al.
2013/0345334 A1 12/2013 Hoogenboom et al.

FOREIGN PATENT DOCUMENTS

GB    0 760 311 A      10/1956
GB    1 164 582 A       9/1969
JP    2005-161698 A     6/2005
WO    WO-00/33764 A1    6/2000
WO    WO-00/71600 A1   11/2000

(Continued)

OTHER PUBLICATIONS

Kelly et al., "Synthesis of Poly (2-oxazoline)-Based Hydrogels with Tailor-Made Swelling Degrees Capable of Stimuli-Triggered Compound Release", Macromol. Rapid Commun., 2011 vol. 32 pp. 1815-1819.
Bentolila, A. et al., "Poly(N-acryl amino acids): A new class of biologically active polyanions", Journal of Medicinval Chemistry, American Chemical Society, vol. 43, Jan. 1, 2000, pp. 2591-2600.
Cesana, et al. "First Poly(2-oxazoline)s with Pendant Amino Groups", Macromolecular Chemistry and Physics, (2006), vol. 207, pp. 183-192.
Chujo, et al. "Reversible Gelation of Polyoxazoline by Means of Diels-alder Reaction", Macromolecules, 1990, vol. 23, pp. 2636-2641.
Diehl Christina et al, "Thermo-responsive polyoxazolines with widely tuneable LCSTa", Database Medline, US National Library of Medicine, Feb. 2009, vol. 9, No. 2, pp. 157-161.

(Continued)

Primary Examiner — Tae H Yoon
(74) Attorney, Agent, or Firm — Foley & Lardner LLP

(57) ABSTRACT

A biocompatible, covalently cross-linked, polymer that is obtained by reacting an electrophilically activated polyoxazoline (EL-POX) with a nucleophilic cross-linking agent is disclosed. The EL-POX comprises m electrophilic groups; and the nucleophilic cross-linking agent comprises n nucleophilic groups, wherein the m electrophilic groups are capable of reacting with the n nucleophilic groups to form covalent bonds; wherein m≥2, n≥2 and m+n≥5; wherein at least one of the m electrophilic groups is a pendant electrophilic group and/or wherein m≥3; and wherein the EL-POX comprises an excess amount of electrophilic groups relative to the amount of nucleophilic groups contained in the nucleophilic cross-linking agent. Biocompatible medical products and kits comprising the cross-linked POX-polymers are also disclosed.

13 Claims, No Drawings

(56) References Cited

FOREIGN PATENT DOCUMENTS

| WO | WO-02/062276 | | 8/2002 |
|---|---|---|---|
| WO | WO-02/102864 | A1 | 12/2002 |
| WO | WO-2004/028404 | | 4/2004 |
| WO | WO-2005/109248 | | 11/2005 |
| WO | WO-2006/034128 | A2 | 3/2006 |
| WO | WO-2006/078282 | A2 | 7/2006 |
| WO | WO-2009/043027 | A2 | 4/2009 |
| WO | WO-2009/089542 | A2 | 7/2009 |
| WO | WO-2009/112402 | A1 | 9/2009 |
| WO | WO-2010/033207 | A1 | 3/2010 |
| WO | WO-2010/043979 | A2 | 4/2010 |
| WO | WO-2010/059280 | | 5/2010 |
| WO | WO-2012/057628 | A2 | 5/2012 |

OTHER PUBLICATIONS

Inata, H. et al., "Postcrosslinking of linear polyesters. II. UV-induced crosslinking agents having carboxyl reactive group", Journal of Applied Polymer Science, vol. 36, No. 7, 1988, pp. 1667-1672.

International Search Report in PCT/NL2012/050001 dated May 16, 2012.

International Search Report in PCT/NL2012/050933 dated May 7, 2013.

International Search Report of PCT/NL2013/050187 dated Apr. 25, 2013.

Liu, et al. "Shell Cross-Linked Micelle-Based Nanoreactors for the Substrate-Selective Hydrolytic Kinetic Resolution of Epoxides", J. Am. Chem. Soc., (2011), vol. 133, 1426001314263.

Luxenhofer, "Novel Functional Poly(2-oxazoline)s as Potential Carriers for Biomedical Applications. Dissertation", (2007), TOC, pp. 167-173 and 248.

Luxenhofer, et al. "Novel Functional Poly(2-oxazoline)s as Potential Carriers for Biomedical Applications. Dissertation", Internet Citation, 2007, XP008138013, http://mediatum2.ub.tum.de/doc/620620/document.pdf. (Table of Contents).

Mero, et al. "Synthesis and characterization of poly(2-ethyl2-oxazoline)-conjugates with proteins and drugs: Suitable alternatives to PEG-conjugates?", Journal of Controlled Release, Oct. 2007, vol. 125, No. 2, pp. 87-95.

Richter, R. et al., "Uber die Umsetzungen von 2-alkyl-Delta2-oxazolinen und 2-methyl-Delta2-thiazolin mit Arylisocyanaten", Liebigs Ann. Chem., vol. 743, 1971, pp. 10-24.

Santini, et al. "Synthesis and Bulk Assembly Behavior of Linear-Dendritic Rod Diblock Copolymers", Journal of Polymer Science: Part A: Polymer Chemistry, (2004), vol. 42, pp. 2784-2814.

Zarka, et al. "Amphiphilic Polymer Supports for the Asymmetric Hydrogenation of Amino Acid Precursors in Water", Chem. Eur. J. (2003), vol. 9, pp. 3228-3234.

* cited by examiner

CROSS-LINKED POLYMERS AND IMPLANTS DERIVED FROM ELECTROPHILICALLY ACTIVATED POLYOXAZOLINE

CROSS-REFERENCE TO RELATED APPLICATIONS

This application is a Divisional Application of U.S. patent application Ser. No. 15/617,009, now U.S. Pat. No. 10,314,936, filed Jun. 8, 2017, which is a Continuation Application of U.S. patent application Ser. No. 13/978,045, filed Sep. 16, 2013, now U.S. Pat. No. 9,770,527, which is the U.S. National Phase of International Patent Application No. PCT/NL2012/050001, filed Jan. 2, 2012, published on May 3, 2012 as WO 2012/057628 A3, which claims priority to European Patent Application No. 11150099.7, filed Jan. 4, 2011. The contents of these applications are herein incorporated by reference in their entirety.

TECHNICAL FIELD OF THE INVENTION

The invention relates to a biocompatible, covalently cross-linked polymer that is obtained by reacting electrophilically activated polyoxazoline (EL-POX) with a cross-linking agent.

The invention further relates to biocompatible medical products comprising such a cross-linked POX-polymer. Examples of such medical products are medical implants including bone implants, soft tissue implants, adhesive implants, coatings on implants, sutures, adhesive tissue sealants and adhesive tissue tapes.

Also provided is a kit for producing a biocompatible, cross-linked POX-polymer.

The invention further provides a tissue adhesive medical product comprising at least 1% by weight of dry matter of electrophilically activated POX comprising reactive groups that are capable of reacting with tissue components.

BACKGROUND OF THE INVENTION

Tissue adhesives have many potential medical applications, including wound closure, supplementing or replacing sutures or staples in surgical procedures, adhesion of synthetic onlays or inlays to the cornea, drug delivery devices, and as anti-adhesion barriers to prevent post-surgical adhesions.

Conventional tissue adhesives include fibrin sealants, cyanoacrylate based sealants, and other synthetic sealants and polymerizable macromers. Some of these conventional sealants are only suitable for a specific range of adhesive applications. For example, cyanoacrylate-based adhesives have been used for topical wound closure, but the release of toxic degradation products limits their use for internal applications. Fibrin-based adhesives are expensive, often need refrigerated storage, are slow curing, have limited mechanical strength, and pose a risk of viral infection.

For certain applications, for example, ophthalmic applications such as sealing wounds resulting from trauma such as corneal lacerations, or from surgical procedures such as vitrectomy procedures, abdominal hernias, cataract surgery, LASIK surgery, glaucoma surgery, and corneal transplants; neurosurgery applications, such as sealing the dura; plugging to seal a fistula or the punctum, slow degrading tissue adhesives are needed.

The last decade, several types of (semi)synthetic hydrogel tissue adhesives have been developed, which have improved adhesive properties and are non-toxic. Most of these hydrogel tissue adhesives, like DuraSeal®, are chemically based on a process called PEGylation used in polymer-modified therapeutics with polyethylene glycol (PEG) end capped mPEG-NHS precursors like, for instance, PEG-succinimidyl glutarate. These hydrogel tissue adhesives, based on PEGylation, typically swell or dissolve away too quickly, or lack sufficient cohesion (interconnecting mechanical strength), thereby decreasing their effectiveness as surgical adhesives. Moreover, to apply these hydrogel tissue adhesives, dual syringe spray technology may be needed, which demands extensive sample preparation from freeze dried starting materials. Finally, the properties of such PEG-based materials cannot be easily controlled and the number of NHS-groups is limited to the number of chain ends; possibly comprising multiple NHS groups per chain end resulting in a high NHS group density rather than regularly distributed groups.

WO 02/062276 describes a hydrogel tissue sealant comprising a star-shaped PEG-succinimidyl glutarate precursor, also known as star-PEG-NHS or star-PEG-NS or star-SG-PEG or star-PEG-SG, that reacts with a trilysine precursor. The star-SG-PEG precursor may be reconstituted in pH 4 phosphate, while the trilysine precursor may be reconstituted in pH 8 borate buffer. Upon mixing, covalent amide bonds between amines of the trilysine precursor and NHS-activated terminal carboxylate groups of the star-SG-PEG precursor are formed.

US 2003/0119985 and US 2005/0002893 describe a tissue sealant based on the same star-PEG-NHS/trilysine principles in which hydrogels are formed by reacting a component having nucleophilic groups with a component having electrophilic groups to form a cross-linked network via covalent bonding.

WO 2010/043979 describes an implant comprising: a porous layer, said porous layer comprising a first sublayer that comprises a first hydrogel precursor and a second sublayer free from hydrogel precursor; and a first additional layer, said first additional layer being a non porous layer comprising a second hydrogel precursor, wherein the first hydrogel precursor has nucleophilic functional groups and the second hydrogel precursor has electrophilic functional groups.

WO 02/102864 describes cross-linkable composition comprised of:
a) a first cross-linkable component A having m nucleophilic groups, wherein m≥2;
b) a second cross-linkable component B having n electrophilic groups capable of reaction with the m nucleophilic groups to form covalent bonds, wherein n≥2 and m+n≥4; and
c) a third cross-linkable component C having at least one functional group selected from (i) nucleophilic groups capable of reacting with the electrophilic groups of component B and (ii) electrophilic groups capable of reacting with the nucleophilic groups of component A, wherein the total number of functional groups on component C is represented by p, such that m+n+p≥5
wherein at least one of components A, B and C is comprised of a hydrophilic polymer, and cross-linking of the composition results in a biocompatible, nonimmunogenic, cross-linked matrix. Polyoxazolines are mentioned as an example of a hydrophilic polymer.

WO 2006/078282 describes a dry powder composition comprised of: a first component having a core substituted with m nucleophilic groups, where m≥2; and a second component having a core substituted with n electrophilic groups, where n≥2 and m+n≥4; wherein the nucleophilic and electrophilic groups are non-reactive in a dry environment but are rendered reactive upon exposure to an aqueous environment such that the components inter-react in the aqueous environment to form a three-dimensional composition. The core of the first or second component can be a hydrophilic polymer. WO 2006/078282 mentions a range of different hydrophilic polymers, including polyoxazolines.

WO 2010/033207 describes a conjugate comprising a residue of a therapeutic peptide moiety covalently attached, either directly or through a spacer moiety of one or more atoms, to a water-soluble, non-peptidic polymer. Polyoxazoline is mentioned as an example of a water-soluble polymer.

WO 2009/043027 describes multiarmed, monofunctional forms of polyoxazolines and conjugates of such polyoxazoline derivatives with drugs. Example 18 describes the coupling of bis-amine with a polyoxazoline with the repeating unit having the structure —[N(COCH$_2$CH$_3$)CH$_2$CH$_2$]$_n$—, in which the terminal nitrogen is bound to methyl and in which the other terminus carries the following electrophilic residue: —OCO$_2$—NHS.

U.S. Pat. No. 5,635,571 describes polyoxazolines comprising a terminal NH$_2$ or OH group and a pendant ester group. A hyperbranched polymer is produced by amidation between the pendant ester group and the chain terminating NH$_2$ or by transesterification between the pendant ester group and the terminating OH group.

Chujo et al. (*Reversible Gelation of Polyoxazoline by Means of Diels-Alder Reaction*, Macromolecules, 1990(23), 2636-2641) describes the preparation of a polyoxazoline hydrogel by means of intermolecular Diels-Alder reaction between furan-modified poly(N-acetylethylenimine) (PAEI) and maleimide-modified PAEI, which were synthesized from the partially hydrolyzed PAEIs by the reaction with furan- or maleimidecarboxylic acid, respectively, in the presence of dicyclohexylcarbodiimide.

Luxenhofer (Thesis: *Novel Functional Poly(2-oxazoline)s as Potential Carriers for Biomedical Applications*, Technische Universität Munchen (2007)) describes poly(2-oxazoline) hydrogels. These hydrogels are prepared by crosslinking a poly(2-methyl-2-oxazoline) comprising aldehyde sidechains with hydrazine or with a poly(2-ethyl-2-oxazoline) comprising amine sidechains. Gelation and swelling was evaluated in aqueous buffers having a pH in the range of 4 to 9.

It is of interest to expand the range of polymers having implant or tissue sealant applications, especially to provide polymers having properties not possessed by PEG-based polymers while being similarly biocompatible.

SUMMARY OF THE INVENTION

The inventors have discovered that a polymer having excellent implant and/or sealing characteristics can be obtained by reacting an electrophilically activated polyoxazoline (EL-POX) that comprises at least two electrophilic groups with a cross-linking agent that comprises two or more nucleophilic groups. The EL-POX employed in the cross-linked polymer comprises at least 1 pendant electrophilic group or, if it does not, it comprises at least 3 terminal electrophilic groups.

In accordance with one embodiment of the present invention, the cross-linked polymer has tissue-adhesive properties due to the fact that it contains unreacted electrophilic groups that are capable of reacting with nucleophile-containing components naturally present in tissue. Thus, the invention provides a tissue-adhesive biocompatible, covalently cross-linked, polymer that is obtained by reacting an EL-POX with a nucleophilic cross-linking agent, said EL-POX comprising m electrophilic groups; and said nucleophilic cross-linking agent comprising n nucleophilic groups, wherein the m electrophilic groups are capable of reaction with the n nucleophilic groups to form covalent bonds; wherein m≥2, n≥2 and m+n≥5; wherein at least one of the m electrophilic groups is a pendant electrophilic group and/or wherein m≥3; and wherein the EL-POX comprises an excess amount of electrophilic groups relative to the amount of nucleophilic groups contained in the nucleophilic cross-linking agent.

The cross-linked polymer of the present invention provides a number of beneficial properties:

Adhesiveness and mechanical properties of the cross-linked polymer can be manipulated effectively by controlling the level and nature of alkyl side chain and/or end-group functionalization and the polymer chain length. Cationic 2-alkyl-2-oxazoline polymerization can suitably be used to incorporate a large number of activated groups in the alkyl side chains of the POX polymer;

Cohesiveness of the cross-linked polymer is determined largely by the number/density of cross-links within the polymer. The number of cross-links in the polymer can be varied within wide ranges by incorporating different amounts of activated groups in the alkyl side chains of the POX;

The swelling index of the cross-linked polymer can be controlled by manipulating the number of cross-links and the chain length of the alkyl side chains in the POX;

Implants made of the cross-linked polymer are an ideal drug depot for local drug delivery. The release of drugs, such as antibiotics, growth factors like VEGF and osteogenic factor (BMP-2), may be sustained by slow diffusion from the interconnecting network depending on the nature of the alkyl side chains and the density of cross links within the network;

Biodegradability of the cross-linked polymer can be controlled effectively by incorporating hydrolysable groups, such as esters or carbonates, into the copolymers. It is further influenced by the number of internal cross links. Thus, it is possible to fine tune the biodegradibility of the polymer to the intended use;

Based on end capped POX-NHS in research for drug delivery, POX seems to have similar or even better stealth and antifouling behaviour than PEG. For renal clearance the POX should have a Mw of 30,000 or less.

Another aspect of the invention relates to a kit for producing a biocompatible, cross-linked polymer, said kit comprising the EL-POX and the nucleophilic cross-linking agent described herein before; wherein at least one of the m electrophilic groups is a pendant electrophilic group. This kit may suitably be used to deliver bone substitute materials, anti-adhesive implants (films), adhesive implants (for instance a tissue sealant for closing arterial puncture sites, or for embolization or to treat urinary incontinence).

The rate at which cross-linking occurs when the EL-POX and cross-linking agent are brought together can be controlled effectively by including non-inert fluids, such as water (pH), alcohols and/or polyols.

The invention also provides a biocompatible medical product comprising at least 1% by weight of dry matter of the tissue-adhesive cross-linked polymer of the present invention. Examples of such biocompatible medical products include implants, tissue sealants, adhesive tissue tape, suture materials, polymer coated stents and haemostatic materials.

The invention further provides a tissue adhesive medical product comprising at least 10% by weight of dry matter of EL-POX, said EL-POX comprising at least 2 electrophilic groups, including at least one pendant electrophilic group, said reactive groups being selected from carboxylic acid esters, sulfonate esters, phosphonate esters, pentafluorophenyl esters, p-nitrophenyl esters, p-nitrothiophenyl esters, acid halide groups, anhydrides, ketones, aldehydes, isocyanato, thioisocyanato (isothiocyanato), isocyano, epoxides, activated hydroxyl groups, olefins, glycidyl ethers, carboxyl, succinimidyl esters, succinimidyl carbonates, succinimidyl carbamates, sulfosuccinimidyl esters, sulfosuccinimidyl carbonates, maleimido, ethenesulfonyl, imido esters, aceto acetate, halo acetal, orthopyridyl disulfide, dihydroxyphenyl derivatives, vinyl acrylate, acrylamide, iodoacetamide and combinations thereof. The aforementioned reactive groups are capable of reacting with nucleophile-containing components naturally present in tissue, thereby imparting tissue adhesive properties to the medical product containing the EL-POX.

The tissue adhesive medical product of the present invention offers the following advantages:
- Due to its hydrophilic/hydrophobic balance, EL-POX is soluble in organic fluids like ethanol and dichloromethane as well as in water.
- EL-POX has excellent amorphous properties with a glass transition temperature markedly higher compared to, for instance, polyethylene glycol.
- EL-POX has film forming capabilities and is easy to plasticize with limited amounts of plasticizers. An advantage of EL-POX over electrophilically activated PEG is the possibility to incorporate different and also functionalized groups along the chain in order to tune the polymer properties for specific applications;
- POX provides a protective environment for NHS groups in the implant when it is not exposed to water or bodily fluids.

DETAILED DESCRIPTION OF THE INVENTION

Accordingly, one aspect of the invention relates to a tissue-adhesive biocompatible, covalently cross-linked, polymer that is obtained by reacting an electrophilically activated polyoxazoline (EL-POX) with a nucleophilic cross-linking agent, said EL-POX comprising m electrophilic groups; and said nucleophilic cross-linking agent comprising n nucleophilic groups, wherein the m electrophilic groups are capable of reaction with the n nucleophilic groups to form covalent bonds; wherein m≥2, n≥2 and m+n≥5; wherein at least one of the m electrophilic groups is a pendant electrophilic group and/or wherein m≥3; and wherein the EL-POX comprises an excess amount of electrophilic groups relative to the amount of nucleophilic groups contained in the nucleophilic cross-linking agent.

The term "polyoxazoline" as used herein refers to a poly(N-acylalkylenimine) or a poly(aroylalkylenimine) and is further referred to as POX. An example of POX is poly(2-ethyl-2-oxazoline). The term "polyoxazoline" also encompasses POX copolymers.

The terminology "pendant electrophilic group" refers to an electrophilic group that is comprised in a side chain, e.g. an alkyl or aryl side chain, of the POX polymer, as opposed to an electrophilic group that is located at a terminus of the POX polymer chain. It should be understood that a particular side chain of the POX polymer may suitably contain more than one electrophilic group, in which case each electrophilic group within that particular side chain counts as a pendant electrophilic group.

The term "amine groups" as used herein refers to primary or secondary amine groups.

Whenever the cross-linked polymer of the present invention is characterized on the basis of the presence of a certain number of particular groups or bonds per 100 monomers it should be understood that this does not imply that the polymer contains at least 100 monomers. For example, a cross-linked polymer comprising 80 monomers and 8 pendant groups contains 10 pendant groups per 100 monomers. Likewise, if a polymer contains 80 monomers and it is specified that this polymer contains, for instance, at least x pendant groups per 100 monomers, this criterion is met if this particular polymer contains on average at least 0.8x pendant groups.

Preferably, the EL-POX of the present invention is an electrophilically activated version of a polyoxazoline polymer whose repeating units are represented by the following formula (I):

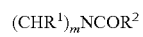

$R^2$, and each of $R^1$ independently being selected from H, optionally substituted $C_{1-22}$ alkyl, optionally substituted cycloalkyl, optionally substituted aralkyl, optionally substituted aryl; and m being 2 or 3. The invention also encompasses the use of polyoxazolines copolymers that comprise two or more different repeating units that are represented by formula (I).

Preferably, $R^1$ and $R^2$ in formula (I) are selected from H and $C_{1-22}$ alkyl, even more preferably from H and $C_{1-4}$ alkyl. $R^1$ most preferably is H. The integer m in formula (I) is preferably equal to 2.

According to a preferred embodiment, the polyoxazoline employed in accordance with the present invention is a polymer, even more preferably a homopolymer of 2-alkyl-2-oxazoline, said 2-alkyl-2-oxazoline being selected from 2-methyl-2-oxazoline, 2-ethyl-2-oxazoline, 2-propyl-2-oxazoline, 2-butyl-2-oxazoline and combinations thereof. Most preferably, the polyoxazoline is a homopolymer of 2-ethyl-oxazoline.

Preferably, the electrophylically active POX (EL-POX) and the cross-linking agent employed in the present cross-linked polymer are not identical.

Then nucleophilic groups of the nucleophilic cross-linking agent are preferably selected from amine groups, thiol groups and combinations thereof. Most preferably, these nucleophilic groups are amine groups.

EL-POX can be activated in its side chains, at its termini (provided it contains at least 3 terminal elecrophilic groups), or both. An example of a terminal, end capped, EL-POX is a succinimidyl succinate ester like $CH_3O-POX-O_2C-CH_2-C(CH_2CO_2-NHS)_3$. An example of a side chain activated EL-POX is POX containing NHS groups in the alkyl side chain. Yet another example of EL-POX are star-shaped polymers end-functionalized with an NHS-esters.

The electrophilic groups contained in the EL-POX preferably are highly reactive towards amine groups or thiol groups, preferably at ambient and/or physiological conditions. Thus, unlike U.S. Pat. No. 5,635,571, the electrophilic groups preferably are not pendant ester groups having the following formula —(CO)R(CO)OR², wherein R is phenylene or alkylene containing 2 to 18 carbon atoms, and R² is $C_{1-4}$ alkyl.

The electrophilic groups present in the EL-POX are preferably selected from: carboxylic acid esters, sulfonate esters, phosphonate esters, pentafluorophenyl esters, p-nitrophenyl esters, p-nitrothiophenyl esters, acid halide groups, anhydrides, ketones, aldehydes, isocyanato, thioisocyanato (isothiocyanato), isocyano, epoxides, activated hydroxyl groups, olefins, glycidyl ethers, carboxyl, succinimidyl esters, succinimidyl carbonates, succinimidyl carbamates, sulfosuccinimidyl esters, sulfosuccinimidyl carbonates, maleimido (maleimidyl), ethenesulfonyl, imido esters, aceto acetate, halo acetal, orthopyridyl disulfide, dihydroxy-phenyl derivatives, vinyl, acrylate, acrylamide, iodoacetamide and combinations thereof.

More preferably, the electrophilic groups present in the EL-POX are selected from: carboxylic acid esters, acid chloride groups, anhydrides, ketones, aldehydes, isocyanato, thioisocyanato, epoxides, activated hydroxyl groups, olefins, carboxyl, succinimidyl ester, succinimidyl carbonate, succinimidyl carbamates, sulfosuccinimidyl ester, sulfosuccinimidyl carbonate, maleimido, ethenesulfonyl and combinations thereof. Even more preferably, the electrophilic groups present in the EL-POX are selected from aldehydes, isocyanato, thioisocyanato, succinimidyl ester, sulfosuccinimidyl ester, maleimido and combinations thereof Most preferably, the electrophilic groups present in the EL-POX are selected from isocyanato, thioisocyanato, succinimidyl ester, sulfosuccinimidyl ester, maleimido and combinations thereof.

Examples of sulfonate esters that can be used as electrophilic groups include mesylate, tosylate, nosylate, triflate and combinations thereof. Examples of olefins that can be employed include acrylate, methacrylate, ethylacrylate and combinations thereof. Examples of activated hydroxyl groups include hydroxyl groups that have been activitated with an activating agent selected from p-nitrophenyl chlorocarbonates, carbonyldiimidazoles (e.g. 1,1-carbonyl diimidazole) and sulfonyl chloride.

According to one preferred embodiment, the nucleophilic groups of the nucleophilic cross-linking agent are amine groups and the electrophilic groups comprised in the EL-POX are selected from carboxylic acid esters, sulfonate esters, phosphonate esters, pentafluorophenyl esters, p-nitrophenyl esters, p-nitrothiophenyl esters, acid halide groups, anhydrides, ketones, aldehydes, isocyanato, thioisocyanato, isocyano, epoxides, activated hydroxyl groups, glycidyl ethers, carboxyl, succinimidyl esters, succinimidyl carbonates, succinimidyl carbamates, sulfosuccinimidyl esters, sulfosuccinimidyl carbonates, imido esters, dihydroxy-phenyl derivatives, and combinations thereof.

Examples of succinimidyl derivatives that may be employed include succinimidyl glutarate, succinimidyl propionate, succinimidyl succinamide, succinimidyl carbonate, disuccinimidyl suberate, bis(sulfosuccinimidyl) suberate, dithiobis(succinimidylpropionate), bis(2-succinimidooxycarbonyloxy) ethyl sulfone and 3,3'-dithiobis(sulfosuccinimidyl-propionate). Examples of sulfosuccinimidyl derivatives that can be used include sulfosuccinimidyl(4-iodoacetyl)aminobenzoate, bis(sulfosuccinimidyl) suberate, sulfosuccinimidyl-4-(N-maleimidomethyl)-cyclohexane-1-carboxylate, dithiobis-sulfosuccinimidyl propionate, disulfo-succinimidyl tartarate; bis[2-(sulfo-succinimidyloxy-carbonyloxyethylsulfone)], ethylene glycol bis(sulfosuccinimiclylsuccinate), dithiobis-(succinimidyl propionate). Examples of dihydroxyphenyl derivatives include dihydroxyphenylalanine, 3,4-dihydroxyphenylalanine (DOPA), dopamine, 3,4-dihydroxyhydrocinnamic acid (DOHA), norepinephrine, epinephrine and catechol.

Even more preferably, the electrophilic groups contained in the EL-POX are selected from aldehydes, succinimidyl esters, succinimidyl carbonates, succinimidyl carbamates, imido esters, dihydroxyphenyl derivatives and combinations thereof. Most preferably, the electrophilic groups are selected from the group of N-hydroxysuccinimide esters, aldehydes, dihydroxyphenyl derivatives and combinations thereof.

According to another preferred embodiment, the nucleophilic groups of the nucleophilic cross-linking agent are thiol groups and the electrophilic groups contained in the EL-POX are selected from halo acetals, orthopyridyl disulfide, maleimides, vinyl sulfone, dihydroxyphenyl derivatives, vinyl, acrylate, acrylamide, iodoacetamide, succinimidyl ester, succinimidyl carbonate, succinimidyl carbamates, sulfosuccinimidyl ester, sulfosuccinimidyl carbonate and combinations thereof. More preferably, the electrophilic groups are selected from succinimidyl esters, halo acetals, maleimides, or dihydroxyphenyl derivatives and combinations thereof. Most preferably, electrophilic groups are selected from maleimides or dihydroxyphenyl derivatives and combinations thereof.

The benefits of the present invention are particularly appreciated in case the number of electrophilic groups m that is contained in the EL-POX is at least 13.

The EL-POX according to the present invention is advantageously derived from a copolymer of 2-NHS-functional-2-oxazoline and 2-alkyl-2-oxazoline. The 2-NHS-functional-2-oxazoline comprised in the copolymer is preferably selected from mercaptoalkanoate NHS-ester functionalized 2-alkenyl-2-oxazoline or 2-NHS alkanoate-2-oxazoline and combinations thereof. Even more preferably, the 2-NHS-functional-2-oxazoline is selected from mercaptoacetic acid NHS-ester functionalized 2-butenyl-2-oxazoline, 2-NHS propionate-2-oxazoline and combinations thereof.

The NHS-ester may already be present in monomers employed during polymer synthesis or it may be introduced afterwards by coupling to a functional comonomer or by partial hydrolysis of POX followed by alkylation or amidation of the resulting secondary amine groups in the polymer chain. The 2-alkyl-2-oxazoline is preferably selected from 2-ethyl-2-oxazoline, 2-methyl-2-oxazoline, 2-propyl-2-oxazoline and combinations thereof. Typically, the EL-POX contains 2-NHS-functional-2-oxazoline and 2-alkyl-2-oxazoline in a molar ratio that lies within the range of 1:33 to 1:2, more preferably of 1:20 to 1:5.

In accordance with another advantageous embodiment the EL-POX according to the present invention is a copolymer of 2-alkyl-2-oxazoline and 2-maleimido-functionalized-2-oxazoline. The latter maleimido unit can be introduced by post-modification of amine or acid side chain functionalities or of backbone secondary amines resulting from partial hydrolysis.

The EL-POX of the present invention advantageously contains one or more pendant electrophilic groups. Typically, the EL-POX contains 3 to 50 pendant electrophilic groups per 100 monomers, more preferably 4 to 35 pendant electrophilic groups per 100 monomers, even more preferably at least 5 to 20 pendant electrophilic groups per 100 monomers.

As explained herein before, more than one electrophilic group may be contained in a side chain of the EL-POX. Preferably, however, the pendant electrophilic groups of the EL-POX are located in different side chains.

The EL-POX employed in accordance with the present invention typically has a molecular weight in the range of 1,000 to 100,000 g/mol, more preferably of 5,000 to 50,000 and most preferably of 10,000 to 30,000 g/mol.

According to a particularly preferred embodiment, the n nucleophilic groups present in the nucleophilic cross-linking agent are primary amine groups.

In one embodiment of the invention the nucleophilic cross-linking agent employed in the cross-linked polymer is a low molecular weight polyamine having a molecular weight of less than 1,000 g/mol, more preferably of less than 700 g/mol and most preferably of less than 400 g/mol. Even more preferably, the nucleophilic cross-linking agent is selected from the group of dilysine; trilysine; tetralysine; pentalysine; dicysteine; tricysteine; tetracysteine; pentacystein; oligopeptides comprising two or more amino acid residues selected from lysine, ornithine, cysteine, arginine and combinations thereof, and other amino acid residues; spermine; tris(aminomethyl)amine; arginine and combinations thereof.

According to another embodiment of the invention, the nucleophilic cross-linking agent employed in the cross-linked polymer is a high molecular weight polyamine selected from the group of: nucleophilically activated POX (NU-POX) comprising at least two amine groups; chitosan; chitosan derivatives (e.g. dicarboxy-derivatised chitosan polymers as described in WO 2009/028965), polyethyleneimines; polyvinylamine; polyallyl amine; amine-functionalized poly(meth)acrylates; polysaccharides containing amine-functional moieties such as poly(galactosamine); styrenics; polypeptides comprising two or more amino acid residues selected from lysine, ornithine, cysteine, arginine and combinations thereof, and other amino acid residues; and combinations thereof. Albumin of natural source or recombinant is an example of a polypeptide that may suitably be employed as a polypeptide. Amine-functionalized polyethylene glycol is another example of a high molecular weight polyamine that can suitably be employed as the nucleophilic cross-linking agent.

The high molecular weight cross-linking agent typically has a molecular weight of at least 2,000 g/mol, even more preferably of at least 10,000 g/mol.

Preferably, the nucleophilic cross-linking agent is not a pharmaceutically active peptide comprising more than five, more preferably more than two amino acid residues (as opposed to the conjugates described in WO 2010/033207). Most preferably, the cross-linking agent is not a pharmaceutically active peptide. Here the term "pharmaceutically active peptide" means that the pharmaceutically activity of the peptide has been demonstrated scientifically.

According to a particularly preferred embodiment the high molecular weight polyamine is NU-POX comprising at least two amine groups. Even more preferably, the high molecular polyamine is derived from a homopolymers or copolymer of cysteamine modified 2-alkenyl-2-oxazoline or 2-t-BOC-aminoalkyl-2-oxazoline and 2-alkyl-2-oxazoline. The cysteamine modified 2-alkenyl-2-oxazoline comprised in the copolymer is preferably selected from 2-butenyl-2-oxazoline, and combinations thereof. The 2-alkyl-2-oxazoline is preferably selected from 2-ethyl-2-oxazoline, 2-methyl-2-oxazoline, 2-propyl-2-oxazoline and combinations thereof. The amine moieties can also be introduced by partial hydrolysis of POX followed by alkylation or amidation of the resulting secondary amine groups in the polymer chain. Typically, the NU-POX contains cysteamine modified 2-alkenyl-2-oxazoline and 2-alkyl-2-oxazoline in a molar ratio that lies within the range of 1:33 to 1:2, more preferably of 1:20 to 1:5.

According to another preferred embodiment, the n nucleophilic groups present in the nucleophilic cross-linking agent are thiol (sulfohydryl) groups.

In one embodiment of the invention the nucleophilic cross-linking agent employed in the cross-linked polymer is a low molecular weight polythiol comprising 2 or more thiol groups having a molecular weight of less than 1,000 g/mol, more preferably of less than 700 g/mol and most preferably of less than 400 g/mol. Even more preferably, the nucleophilic cross-linking agent is selected from the group of trimercaptopropane, ethanedithiol, propanedithiol, 2-mercaptoethyl ether, 2,2'-(ethylenedioxy)diethanethiol, tetra(ethylene glycol) dithiol, penta(ethylene glycol) dithiol, hexaethylene glycol dithiol; thiol modified pentaerythritol, dipentaerythritol, trimethylolpropane or ditrimethylolpropane; oligopeptides containing at least two cysteine units.

According to another embodiment of the invention, the nucleophilic cross-linking agent employed in the cross-linked polymer is a high molecular weight polythiol selected from the group of: NU-POX comprising at least two thiol groups; thiol-functionalized poly(meth)acrylates; polysaccharides containing thiol-functional moieties; styrenics; polypeptides comprising two or more thiol groups.

According to a particularly preferred embodiment the high molecular weight polythiol is NU-POX comprising at least two thiol groups. Even more preferably, the high molecular polythiol is a poly(2-alkyl-2-oxazoline) with thiol terminal groups that have been introduced by endcapping the polymerization with a multifunctional initiator with potassium xanthogenate followed by aminolysis to get the free thiol gropus. Alternatively, the thiol moieties are introduced into the side chains of the NU-POX by copolymerization of a protected thiol containing monomer or by modification of acid, amine or alkenyl side chains or by modification of the backbone secondary amines resulting from partial hydrolysis. The 2-alkyl-2-oxazoline is preferably selected from 2-ethyl-2-oxazoline, 2-methyl-2-oxazoline, 2-propyl-2-oxazoline and combinations thereof.

The NU-POX typically has a molecular weight in the range of 1,000 to 100,000 g/mol, more preferably of 10,000 to 30,000 g/mol.

According to a particularly preferred embodiment the m electrophilic groups comprised in the EL-POX component of the cross-linked polymer are capable of reacting with the n nucleophilic groups of the cross-linking agent under ambient and/or physiological conditions to form covalent bonds. Most preferably, the electrophilic groups are capable of reacting with the nucleophilic groups to form covalent bonds under ambient condition. The ability to form cross-links at ambient temperature is especially advantageous if the cross-linking should occur in situ during e.g. surgery. Typically, at 35° C. and 1 atm., the cross-linking reaction between the EL-POX and the cross-linking agent is completed within 30 minutes, preferably within 10 minutes, more preferably within 5 minutes, most preferably within 2 minutes.

As explained herein before, for certain applications it can be advantageous if the cross-linked polymer contains free electrophilic groups that have not reacted with the nucleophilic groups of the nucleophilic cross-linking agent. Such a cross-linked polymer is obtained by employing EL-POX comprising an excess amount of electrophilic groups relative to the amount of nucleophilic groups contained in the cross-linking agent. Thus, in a preferred embodiment, the ratio m/n exceeds 1.2, more preferably exceed 1.5, most preferably exceeds 2.0. Typically, the latter ratio does not exceed 1000, more preferably it does not exceed 200, even more preferably it does not exceed 50 and most preferably it does not exceed 10.

The non-reacted electrophilic groups in the cross-linked polymer of the present invention impart tissue adhesive properties to the polymer as they can react with nucleophilic groups (e.g amino groups and thiol groups) that are naturally present in tissue. Thus, when a cross-linked polymer containing non-reacted electrophilic groups is applied to tissue, the non-reacted electrophilic groups can react with nucleophilic groups of the tissue, thereby creating strong adhesion between the polymer and the tissue.

The tissue adhesive properties of the cross-linked polymer can be controlled very effectively by manipulating the number of non-reacted electrophilic groups in the cross-linked polymer. Generally speaking, the higher the number of non-reacted electrophilic groups, the stronger the adhesion.

Thus, in accordance with a particularly preferred embodiment of the invention the cross-linked polymer comprises, per 100 monomers, at least 1, more preferably in between 2 and 95, even more preferably in between 5 and 70, most preferably in between 10 and 50 electrophilic groups that are contained in the EL-POX component of the cross-linked polymer and that have not reacted with a nucleophilic group of the nucleophilic cross-linking agent.

Of the total number of reacted and non-reacted elecrophilic groups in the cross-linked polymer the non-reacted electrophilic groups preferably represent 10-95%, more preferably 20-80% and most preferably 40-60%.

The cross-linked polymer is typically obtained by reacting the EL-POX with the nucleophilic cross-linking agent in a molar ratio of 50:1 to 1:1, more preferably in the range of 10:1 to 3:2

Advantageously, 3-50%, more preferably 4-35% and most preferably 5-20% of the side chains of the EL-POX contain an electrophilic group. As explained herein before, cross-linked polymers obtained by cross-linking an EL-POX having a number of pendant electrophilic groups, as opposed to cross-linked polymer that are obtained by cross-linking an EL-POX with only terminal electrophilic groups, offer a number of advantages, including the possibility to tune characteristics such as cohesion, mechanical strength, swellabilty, biodegradability and a stickiness across much wider ranges than is possible with polymers that have been end-capped with electrophilic groups. In this respect is noted that electrophilically activated PEG, which is described in a large number of prior art publications related to medical implants, does not contain any side chains that enable the incorporation of pendant elecrophilic groups.

The ability of the (dry) cross-linked polymer to swell when contacted with water depends strongly on the level of cross-linking. The more cross linking, the lower the swelling index. Preferably, the polymer contains, per 100 monomers, not more than 50, more preferably not more than 20 and most preferably not more than 10 of covalent bonds that have been formed by the reaction between the electrophilic groups of the EL-POX and the nucleophilic groups of the cross-linking agent. Typically, this number of covalent of bonds is at least 2 per 100 monomers.

The EL-POX employed in the present cross-linked polymer typically has a molecular weight of at least 1,000 g/mol, more preferably of 5,000-100,000 g/mol and most preferably of 10,000-30,000 g/mol.

EL-POX comprising pendant electrophilic groups and NU-POX comprising pendant nucleophilic groups can suitably be prepared by cationic polymerization of the 2-oxazoline monomers initiated by various electrophilic species, for example alkyl halides, sulfonic esters, strong acids and others. POX-derivatives containing activated groups in the side chain can be prepared directly from the 2-oxazoline monomer containing the required group, or by a polymer analogous reaction of polymer precursors. Preparation of POX containing hydroxyl, amino, carboxyl, mercapto, and aldehyde groups in the side chain has been described in literature.

Synthesis of a functional group at the POX terminus is, for instance, described by Anna Mero et. al. (*Synthesis and characterization of poly*(2-*ethyl* 2-*oxazoline*)-conjugates with proteins and drugs: Suitable alternatives to PEG-conjugates?, Journal of Controlled Release 125 (2008) 87-95).

The EL-POX employed in accordance with the present invention can be a homopolymer or a copolymer. Most preferably, EL-POX is a copolymer.

An EL-POX copolymer, notably an amphiphilic copolymer, can be prepared in several different ways. It is feasible, for instance, to polymerize 2-oxazolines containing an (protected) electrophilic or nucleophilic group with a hydrophilic or lipophilic comonomer. It is also possible to partially hydrolyze POX followed by modification of the resulting secondary amine groups in the polymer. Another type of polymer can be prepared by block copolymerizations of activated 2-alkyl-2-oxazolines with other polymers such as polylactides, polycaprolactone or polyethyleneglycol.

Copolymers of EL-POX containing ethyl and NHS groups in the alkyl side chain can be synthesized by cationic polymerization of 2-ethyl-2-oxazoline (ETOX) and 2-(3-butenyl)-2-oxazoline (BUTOX) to yield a poly[2-(ethyl/3-butenyl]-2-oxazoline copolymer. This poly[2-(ethyl/3-butenyl)-2-oxazoline copolymer can be functionalized with 3-mercaptopropionic-N-hydroxysuccinimide ester or in a two-step approach by first thiol-ene coupling of mercaptopropionic acid followed by activation with NHS to synthesize NHS-side chain activated poly[2-(ethyl/3-butenyl)]-2-oxazoline copolymer.

NU-POX containing ethyl and amino (—$NH_2$) groups in the alkyl side chain can be synthesized in a similar fashion by reaction of poly[2-(ethyl/3-butenyl)]-2-oxazoline copolymer with cysteamine or by partial hydrolysis of POX followed by post-modification.

NU-POX containing ethyl and thiol (—SH) groups in the alkyl side chain can be prepared in a similar fashion by reaction of poly[2-(ethyl/3-butenyl)]-2-oxazoline copolymer with an excess of ethanedisulfide or by copolymerization of 2-ethyl-2-oxazoline with a monomer bearing a protected thiol group.

In case the present cross-linked polymer is obtained by cross-linking an NHS-activated EL-POX, biodegradability can range from essentially non-degradable to easily degradable. Biodegradability can be improved by incorporation of an ester link that is more readily hydrolyzed than the secondary amides resulting from reactions between the NHS-ester and amines. The esters are slowly hydrolyzed in aqueous environment while the secondary amides are mainly hydrolyzed by enzymatic degradation that will be very slow in the cross-linked network.

Cationic polymerization enables the synthesis of copolymers with a predefined number of activated groups. Furthermore, cationic 2-alkyl-2-oxazoline polymerization can be used to incorporate a large number of active groups as these active groups are coupled to the numerous alkyl side chains of the POX. This again makes it possible to produce highly cross-linked polymers with excellent cohesive properties as well as outstanding adhesive properties in case the cross-linked polymer has a high density of unreacted electrophilic groups.

In addition, cationic polymerization allows the incorporation of various functional groups in the side-chain and/o terminus, thereby enhancing the versatility of the POX polymer system.

The synthesis of a copolymer containing a predefined number of activated groups per copolymer can be carried out as follows: a copolymer is synthesized by cationic polymerization of ETOX and BUTOX, as described previously, to yield a poly[2-(ethyl/3-butenyl)-2-oxazoline copolymer. Upon functionalization with 3-mercaptopropionic-N-hydroxysuccinimide ester (either directly or in two steps by first introducing mercaptopropionic acid followed by NHS activation) via radical thiol-ene coupling, NHS activated side chains are introduced. In case the initial ETOX/BUTOX molar ratio is 90/10, the percentage of reactive groups per poly[2-(ethyl/3-butenyl)]-2-oxazoline copolymer, will be 10%. Increasing the BUTOX in the initial 90/10 ETOX/BUTOX mixture will eventually result in a higher percentage of —NHS groups, i.e. more than 10%. The exact number of incorporated NHS groups can be controlled by the ratio of monomer to initiator that determines the length of the polymer. For example, using an ETOX/BUTOX ratio of 90/10 and a monomer to initiator ratio of 100:1 yields polymers with 100 repeat units comprising 10 NHS groups. When the monomer to initiator ratio is changed to 200:1 the resulting copolymer will have 20 NHS groups with the same ETOX/BUTOX ratio. A similar procedure van be followed for the synthesis of POX-maleimide, whereby a thiol-modified maleimide (furan protected) is added to the poly[2-(ethyl/3-butenyl)-2-oxazoline copolymer by radical thiol-ene coupling. Deprotection of the furan-maleimide yields the POX-maleimide as EL-POX.

The cross-linked polymer of the present invention may be biodegradable or non-biodegradable. Preferably, the polymer is biodegradable.

A further aspect of the invention relates to a biocompatible medical product comprising at least 1%, preferably at least 25% and most preferably 50-100% by weight of dry matter of a tissue-adhesive cross-linked polymer as defined herein before. Examples of such medical products include implants, tissue sealants, adhesive tissue tape, adhesive tissue film, suture material, polymer coated stents and haemostatic (porous) materials.

EL-POX, the cross-linking agent and combinations of EL-POX and the cross-linking agent can be formed into shape by solvent casting or hot melt extrusion leading to, for instance, an amorphous film or tape. The reaction between electrophilic groups of the EL-POX and the nucleophilic groups of the crosslinking agent results in cross-linking and the excess of electrophilic groups enables the cross-linked polymer to form links to tissue. Thus, the present invention enables the preparation of medical products that combine cohesiveness with adhesiveness.

A very important property of POX films is that upon thorough drying they protect the interior from hydrolysis. Thus, excess (non-reacted) electrophilic groups in the EL-POX or in the crosslinked polymer will retain their activity upon storage. When a medical product containing non-reacted electrophilic groups is applied to tissue an electrophilic-nucleophilic reaction will occur between these electrophilic groups and nucleophilic reactants, notably amino or thiol groups present in tissue, thereby forming a cross linked external network (adhesion) via covalent bonding. Accordingly, the medical product advantageously contains less than 10%, even more preferably less than 5% and most preferably less than 1% water by weight of the cross-linked polymer.

The medical product preferably also contains not more than a limited amount of organic solvent. Preferably, the product contains less than 5%, more preferably less than 0.5% organic solvent by weight of the cross-linked polymer.

For e.g. a tissue sealing tape, EL-POX and cross-linking agent can be mixed in any ratio needed by solvent casting or hot melt extrusion. This approach enables very precise fine tuning of the properties needed for an adhesive tissue tape. In case the amount of electrophilic groups in the EL-POX is high and the number of nucleophilic groups provided by the cross-linking agent is relatively low, cohesion of the resulting cross-linked polymer will be low and adhesion to tissue will be high. Naturally, it is also feasible to produce an adhesive tissue tape with high cohesion and high adhesion by combining a relatively high amount of cross-linking agent with an excess amount of electrophilic groups in the EL-POX.

A particularly advantageous embodiment of the present medical product is an adhesive tissue tape or an adhesive tissue film. The present invention enables the preparation of a tape or film with excellent tissue-adhesive properties due to the presence of non-reacted electrophilic groups that are capable of reacting with nucleophilic groups naturally present in tissue. Furthermore, the cross-linked polymer of the present invention, due to its amorphous properties and tunable glass transition temperature, enables the preparation of cohesive, flexible and resilient tapes and films as well as tough and harder materials tailor-made for specific applications.

As explained herein before it is highly advantageous if the cross-linked polymer contained in the medical product is in an amorphous state. The term "amorphous" refers to a material that is a solid and in which there is no long-range order of the positions of the molecules. This lack of order distinguishes amorphous solids from crystalline solids.

It is further preferred that the cross-linked polymer has a glass transition temperature of at least −50° C., more preferably at least 0° C. and most preferably at least 20° C. Typically, the glass transition temperature of the polymer does not exceed 120° C.

The adhesive tissue tape of adhesive tissue film of the present invention offers the advantage that it can absorb substantial quantities of water to form a cohesive hydrogel. The absorption of water may result in significant swelling of the product. However, it is also possible to design the product in such a way that it does not swell significantly when it is brought into contact with moisture.

In accordance with one advantageous embodiment, the medical product does not exhibit significant swelling when it comes into contact with moisture. Typically, such a medical product has a swelling index of not more than 100%, preferably of not more than 30% and most preferably of not more than 10%. Medical products having a low swelling index can suitably be applied in repair of dural defects and spinal cord repair In accordance with another preferred embodiment, the medical product shows significant swelling when it is allowed to absorb water. Typically, such a swellable product has a swelling index of 100-1000%. A medical product having a high swelling index may suitably be used to stem blood, e.g. during or after surgery.

The swelling index is determined by recording the exact weight of a sample of about 2 g of fully swollen material. Next, the swollen materials is immersed into 20 mL of PBS buffer and incubated for 24 hours at 37° C. in an air forced oven. Next, the material is dried with paper towel and weighed. Swelling is calculated based on the following formula:

$$\text{Swelling Index \%} = (W_t - W_o)/W_o \times 100$$

where:

$W_o$ is the pre-incubation weight of the swollen material; and $W_t$ is the post-incubation weight of the swollen material.

Greater cross-linking creates a tighter network, which will decrease swelling. This can be advantageous in certain applications, for example, if the medical product is an implant, a suture material or a tissue sealant that is applied in tight locations where gel swelling can potentially cause adverse effects. In that case, the swelling index preferably does not exceed 50%, most preferably it does not exceed 10%.

The present invention enables the preparation of an adhesive tissue tape or tissue film having excellent properties without requiring, for instance, support layers. Accordingly, the adhesive tissue tape preferably is a single layer tape. Likewise, the adhesive tissue film preferably is a single layer film.

In accordance with another advantageous embodiment, the present medical product is an implant. According to a particularly preferred embodiment, the crosslinked polymer contained in the implant provides a matrix to support tissue regeneration. Preferably, this is a biodegradable three-dimensional bioresorbable porous construct with attaching properties to bone material and appropriate mechanical properties to guide cellular attachment and subsequent tissue formation. For bone reconstruction, the construct is preferably also load bearing, meaning that any fluid component in the implant, or the in-situ formed implant, should be kept as low as possible. In this respect it is advantageous that only very limited amounts of plasticizers like triacetin or water are needed to render the EL-POX and NU-POX extrudable.

According to a particularly preferred embodiment, the polymer network comprised in the present implant contains osteoconductive fillers like bone graft materials, including autologous bone, autologous bone particulate, allogenic bone graft material, human cadaver bone, xenograft bone graft material, animal bone, growth factors or synthetic materials such as hydroxyapatite, tricalcium phosphate and bioactive glass.

Another aspect of the invention relates to a kit for producing a biocompatible, cross-linked polymer of the present invention, said kit comprising the EL-POX and the nucleophilic cross-linking agent as defined herein before. Preferably, at least one of the m electrophilic groups of the EL-POX is a pendant electrophilic group.

Independently, the EL-POX and the nucleophilic cross-linking agent may be provided in the form of fluid or a powder. If provided in powder form, the powder should be readily dispersible in a fluid which may be contained within the same kit.

The cross-linked polymer that can be produced with the present kit may or may not have tissue-adhesive properties. For some applications it is beneficial if the kit can be used to produce a cross-linked polymer with tissue-adhesive properties. Thus, advantageously, the EL-POX contained in the present kit comprises an excess amount of electrophilic groups relative to the amount of nucleophilic groups contained in the nucleophilic cross-linking agent. Thus, the EL-POX and the nucleophilic cross-linking agent can react to form a tissue-adhesive cross-linked polymer as defined herein before.

In a preferred embodiment, the kit comprises separately packaged volumes of the EL-POX and the nucleophilic agent. In order to allow the EL-POX and the cross-linking agent to undergo a rapid cross-linking reaction, it is preferred to provide both the EL-POX and the cross-linking agent in the form of a fluid. More specifically, it is preferred that the EL-POX is contained in a first solvent in a concentration of 1-95 wt. % and that the nucleophilic cross-linking agent is contained in a second solvent in a concentration of 1-95 wt. %.

According to a particularly preferred embodiment, the first solvent and the second solvent are selected from water, polyols, alcohols (e.g. ethanol or iso-propanol) and combinations thereof. The volume containing EL-POX and/or the volume containing the cross-linking agent advantageously contains polyol, water or a mixture of both. Furthermore, the latter volumes may suitably be buffered. The solvent(s) and buffering system employed in the present kit are suitable chosen so as to achieve an optimum cross-linking rate.

Polyols that can suitably be employed in the present kit include glycerol, diacetin, triacetin, sorbitol and combinations thereof.

According to a particularly preferred embodiment the first solvent and the second solvent contain 5-50 wt. % water, more preferably 10-30 wt. % water and most preferably 15-20 wt. % water.

In-situ cross-linking characteristics can be improved by plasticizing EL-POX, and optionally NU-POX, with a plasticizer selected from the group of triacetin, glycerol, triethylamine and combinations thereof. Typically, the plasticizer is employed in a concentration of 1-50%, more preferably 3-15% by weight of the EL-POX and/or NU-POX.

The separately packaged volumes of the EL-POX and the nucleophilic agent may suitably contain a pH modifier. An acidulant is advantageously employed in accordance with the present invention to shift the micro-environmental pH of the EL-POX containing volume or the cross linked EL-POX-formulations to more acidic conditions in the presence of water or bodily fluids. The term "micro-environmental pH" refers to the pH within and in the vicinity of the EL-POX of the cross linked EL-POX-formulations.

Examples of acidulants that may suitably be employed include organic and inorganic components that are capable of releasing protons, for example an organic or inorganic acid, an acidic polymer, e.g. a carbomer, or a latent acid (e.g. glucono-δ-lactone). Preferably, the acidulant has a $pK_a$ at 25° C. of 1 to 7, in particular of 2 to 6.5, more particularly of 3 to 6.5.

The pH of the separately packaged volume containing the EL-POX preferably lies in the range of 2-7, more preferably of 3-6, most preferably of 4-5.

The separately packaged volume containing the nucleophilic agent preferably contains an alkalinizing agent that shifts the micro-environmental pH of the nucleophilic agent containing volume to more alkaline conditions in the presence of water or bodily fluids.

Examples of suitable alkalinizing agents include ammonia solution, ammonium carbonate, alkali metal salts including alkali metal carbonates (for instance potassium carbonate and sodium carbonate), potassium hydroxide, sodium hydroxide and sodium borate (borax), or tertiary amines such as triethylamine, triethanolamine or other amines like diethanolamine and monoethanolamine.

Preferably, the alkalinizing agent has a p$K_a$ at 25° C. of 8-14, in particular of 8.5-11, more particularly of 9 to 11.

The pH of the separately packaged volume containing the nucleophilic agent preferably lies in the range of 7-12, more preferably of 8-11, most preferably of 9-10.

The separately packaged volumes EL-POX and cross-linking agent are advantageously contained within a dispensing means from which both volumes can be dispensed simultaneously. Thus, the two cross-linking agents may be delivered simultaneously and a cross-linked polymer will form in situ. By simultaneously dispensing the two reactants and delivering them at the site where they cross-linking should occur, pre-mixing can be avoided and premature cross-linking is effectively prevented. Examples of suitable dispensing means include spray dispensers, syringes, and dual syringes. Syringes suitably comprise a static mixer that ensures that the two reactants are mixed together when simultaneously expelled from said syringe.

In accordance with a preferred embodiment at least one of the separately packaged volumes contains a visualization agent to enhance the visibility. The visualization agent (e.g. a colourant) reflects or emits light at a wavelength detectable to a human eye. Because of the inclusion of the visualization agent it is easy for users to accurately apply the reactive mixture. Examples of suitable colourants include FD&C and D&C colorants, such as FD&C Violet No. 2, FD&C Blue No. 1, D&C Green No. 6, D&C Green No. 5, D&C Violet No. 2; and natural colorants such as beetroot red, canthaxanthin, chlorophyll, eosin, saffron, carmine, indocyanine green, or colored dyes normally found in synthetic surgical sutures. Similarly, dyes such as fluoroscein and methylene blue can be used. The visualization agent may or may not become chemically bound to the hydrogel.

In an alternative embodiment, the kit comprises a first biocompatible thin film containing the EL-POX and a second biocompatible thin film containing the nucleophilic cross-linking agent. The two films may suitably be applied after combining the two films on top of each other. Films may suitably have been perforated to increase their specific surface area.

The biocompatible thin film containing the nucleophilic cross-linking agent preferably comprises an alkalinizing agent as defined herein before.

In accordance with another alternative embodiment, the kit comprises particles having a weight averaged mean diameter of 0.01-1000 μm, said particles including particles containing EL-POX and particles containing the nucleophilic cross-linking agent. The EL-POX and the nucleophilic cross-linking agent may be contained in the same particles or they may be contained in different particles within the same powder.

The aforementioned powder may suitably be used as a haemostatic powder that can be stored under ambient conditions.

Besides the EL-POX and/or the nucleophilic cross-linking agent, the particles comprised in the haemostatic powder may suitably contain a carrier, preferably a water-soluble carrier. Examples of carriers that may suitably be employed include monosaccharides; di- and oligosaccharides, such as lactose, mannitol, trehalose, erythritol, xylitol, sorbitol, maltitol, isomalt, maltodextrin, cellobiose, glucose, fructose, maltulose, lactulose, maltose, gentobiose, isomaltose, lactitol, palatinitol, dulcitol, ribitol, sucrose, raffinose, gentianose, planteose, verbascose, stachyose, melezitose, inositol; and polysaccharides, such as dextran, starch (amylose, amylopectin), glycogen, cellulose, chitin, alginates, callose, chrysolaminarin, xylan, arabinoxylan, mannan, fucoidan and galactomannan; and combinations of these carbohydrates. Preferably, the carrier employed has a glass transition temperature of at least 0° C., more preferably of at least 25° C.

Typically, the haemostatic powder contains 25-75 wt. % of the EL-POX, 25-75 wt. % of the nucleophilic cross-linking agent and 0-50 wt. % of carrier.

Yet another aspect of the invention relates to a tissue adhesive medical product comprising at least 1%, preferably at least 50% and most preferably at least 90% by weight of dry matter of EL-POX, said EL-POX comprising at least 2 electrophilic groups, including at least one pendant electrophilic group, said reactive groups being selected from carboxylic acid esters, sulfonate esters, phosphonate esters, pentafluorophenyl esters, p-nitrophenyl esters, p-nitrothiophenyl esters, acid halide groups, anhydrides, ketones, aldehydes, isocyanato, thioisocyanato, isocyano, epoxides, activated hydroxyl groups, olefins, glycidyl ethers, carboxyl, succinimidyl esters, succinimidyl carbonates, succinimidyl carbamates, sulfosuccinimidyl esters, sulfosuccinimidyl carbonates, maleimido, ethenesulfonyl, imido ester, aceto acetate, halo acetal, orthopyridyl disulfide, dihydroxyphenyl derivatives, vinyl acrylate, acrylamide, iodoacetamide and combinations thereof. The electrophilic groups in the EL-POX may suitably be selected from carboxylic acid esters, acid chloride groups, anhydrides, ketones, aldehydes, isocyanato, thioisocyanato, epoxides, activated hydroxyl groups, olefins, carboxyl, succinimidyl ester, succinimidyl carbonate, succinimidyl carbamates, sulfosuccinimidyl ester, sulfosuccinimidyl carbonate, maleimido, ethenesulfonyl and combinations thereof.

Preferably, the electrophilic groups in the EL-POX are selected from aldehydes, imido esters, isocyanato, thioisocyanato, succinimidyl derivatives, sulfosuccinimidyl derivatives, dihydroxyphenyl derivatives, halo acetals, orthopyridyl disulfide, maleimides, vinyl sulfone and combinations thereof.

Even more preferably, the electrophilic groups contained in the EL-POX are selected from aldehydes, succinimidyl esters, succinimidyl carbonates, succinimidyl carbamates, imido esters, dihydroxyphenyl derivatives, halo acetals, maleimides and combinations thereof.

Most preferably, the electrophilic groups are selected from the group of N-hydroxysuccinimide esters, aldehydes, maleimides, dihydroxyphenyl derivatives and combinations thereof.

In accordance with this particular embodiment of the invention it is preferred that the EL-POX contained in the tissue adhesive medical product has not, or only partially, been cross-linked. Most preferably, the EL-POX contained in the tissue adhesive medical product has not been cross-linked.

The tissue adhesive product of the present invention may comprise a nucleophilic cross-linking agent as defined herein before. It is preferred that the number of reactive nucleophilic groups provided by said cross-linking agent is significantly lower than the number of reactive electrophilic groups contained in the EL-POX. Thus, it is ensured that sufficient numbers of electrophilic groups will remain after the cross-linking reaction between EL-POX and the nucleophilic cross-linking agent to provide adhesion between the cross-linked polymer and e.g tissue. This advantageous embodiment may be realized, for instance, by plasticizing EL-POX and the nucleophilic cross-linking agent into a single film or tape. Before application as a tissue tape, the latter tape may be combined with another water soluble film containing an activator, or a fluid or a spreadable composition containing an activator.

In accordance with a particularly preferred embodiment, the tissue adhesive medical product comprises at least 1%, preferably at least 50% and most preferably at least 75% by weight of dry matter of EL-POX and at least 1%, preferably at least 50% and most preferably at least 75% by weight of dry matter of NU-POX. Advantageously, EL-POX and NU-POX together represent at least 75 wt. %, more preferably at least 95 wt. % of the dry matter contained in the tissue adhesive product.

The combined use of EL-POX and NU-POX in the tissue adhesive medical product offers the advantage that the product can be produced in the form of an amorphous film, tape or powder, e.g. by melt extrusion.

An advantage associated with employing a combination of EL-POX and NU-POX in non-crosslinked form lies in the fact that it enables the preparation of very flexible films or tapes that area easily applied during surgery. Furthermore, the EL-POX and NU-POX will rapidly react to form a cross-linked polymer as soon as water is absorbed by the tissue adhesive medical product (e.g. film or tape), thereby providing excellent sealing properties.

In accordance with another embodiment, the tissue adhesive medical product comprises no nucleophilic cross linking agent. The EL-POX may suitably be embedded in a matrix of other (non-reactive) film forming polymers, including polyoxazolines such as polyethyloxazoline, polymethyloxazoline or polypropyloxazoline. Preferably, the adhesive medical product in accordance with this embodiment comprises 10-95%, more preferably 30-80% and most preferably 50-70% EL-POX by weight of dry matter. The other film forming polymers, preferably represent 5-90%, more preferably 20-70% and most preferably 30-50% of the dry matter contained in the adhesive medical product.

The EL-POX comprised in the tissue adhesive medical product preferably contains at least 2 electrophilic groups per 100 monomers, more preferably at least 5 electrophilic groups per 100 monomers, even more preferably 10-80 electrophilic groups per 100 monomers and most preferably 10-50 electrophilic groups per 100 monomers.

Examples of tissue adhesive medical products that are encompassed by the present invention include adhesive tissue tape, tissue sealant, haemostatic porous material and implants.

Medical products in the form of a tape or film may suitably comprise a polymer matrix comprising the EL-POX and a water-insoluble backing membrane. The use of a backing membrane or film ensures that the EL-POX does not induce unwanted adhesions as the covalent attachment to surrounding tissue will be prevented. The backing membrane may be made of any suitable biocompatible polymer. Preferably, the backing membrane is made of a biocompatible polymer containing primary amines as these will covalently link to the EL-POX.

The crosslinked polymer according to the present invention, the EL-POX as well as the NU-POX may advantageously contain an antimicrobial agent covalently bound to one of the oxazoline unit comprised therein. More preferably, the crosslinked polymer or EL-POX contains an antimicrobial agent that is covalently bound to oxazoline units through an amide or imide group. Examples of antimicrobial agents include aminophenols, aminocresol, amino resorcinol and aminonaphtol. The antimicrobial agent may suitably be bound to the POX-polymer via a spacer group, such as an alkylene, oxyalkylane or silicone. By covalently binding an antimicrobial agent to the POX-polymer it can be ensured that the antimicrobial agent is slowly released during biodegradation of the polymer.

A further embodiment of the present invention provides a composition comprising an adhesive film containing:
 a polymeric material selected from EL-POX, the EL-POX derived biocompatible, covalently cross-linked polymer according to the present invention and combinations thereof; and
 one or more dihydroxyphenylalanine (DHP) derivatives.

The DHP derivatives are preferably selected from 3,4-dihydroxyphenylalanine (DOPA), dopamine, 3,4-dihydroxyhydrocinnamic acid (DOHA), catechol, and combinations thereof.

Typically, the adhesive film contains at least 1%, more preferably at least 25%, most preferably 50-100% of the polymeric material by weight of dry matter.

The DHP content of the adhesive film typically lies in the range of 10-95%, more preferably 20-80% and most preferably 40-60% by weight of dry matter.

The water content of the adhesive film preferably does not exceed 5 wt. %, more preferably it does not exceed 1 wt. %.

The composition may suitably further comprise one or more additive components selected from fillers, oxidants, crosslinkers, microgels, additional polymers, drugs and other therapeutic agents.

The adhesive film may consist of a single layer or it may be composed of a plurality of layers.

The reaction between tissue-reactive electrophilic groups and functional groups on the surface of the tissue may vary with pH. It may therefore be preferable to buffer the tissue surface immediately prior to application or, more preferably, to include a buffer in the product containing covalently cross-linked polymer with reactive elecrophilic groups and/or EL-POX. In the case such product is, for instance, an adhesive film or tape, it may be advantageous to include a buffer in the tissue-contacting layer of the film or tape. The adhesion of such products may be improved by buffering the tissue surface of the product with a buffer having a pH in the range of 9.0-12.0, especially of 9.5-11.5.

The medical products according to the present invention may advantageously be used in a variety of surgical applications. Examples of these surgical applications are summarized below.

| | |
|---|---|
| Neurosurgery | Repair of dural defects; repair of central nervous system tissue; spinal cord repair; nerve grafting; intervertebral disc surgery and cerebrospinal fluid leaks (CSF leaks). |
| Ophthalmic surgery | Clear corneal cataract surgery; laser in situ keratomileusis (LASIK) surgery; corneal ulcer treatment; corneal transplantation; conjunctival repair; retinal attachment; punctal plugging for treatment of dry eyes; oculoplastics and blepharoplasty (eyelid lifts); vitrectomy closure and attachment of extraocular muscles. |

| | |
|---|---|
| Ear, nose and throat surgery | Control of epistaxis (nosebleeds); repair of vocal cord defects; tympanoplasty for repair of perforated eardrum; myringotomy (eardrum incision for drainage) with tube insertion; sinus surgery; nasal reconstructive surgery; tonsillectomy surgery and adenoidectomy surgery. |
| Head and neck surgery | Salivary gland removal; lymph node dissection and treatment of chylous leakage after neck dissection. |
| Interventional radiology | Therapeutic embolization and femoral artery closure during interventional procedures. |
| Vascular surgery | Arteriovenous fistula repair, aortic aneurysm repair and vascular anastomosis. |
| Cardiovascular surgery | Cardiac valve repair; repair of ventricular wall rupture; coronary artery anastomosis during bypass surgery; pacemaker and lead placement; aortic anastomosis and treatment of aortic dissection. |
| Thoracic surgery | Lung lobectomy; lung biopsy and pneumothorax treatment. |
| Gastrointestinal surgery | gastrointestinal anastomosis; peptic ulcer treatment; treatment of esophageal rupture; gallbladder or bile duct anastomosis; gastric bypass surgery; appendectomy; cholecystectomy (gallbladder removal); pancreatic surgery; gastrointestinal fistula repair; sealing of peritoneal dialysis catheter leakage, treatment of abdominal hernias and prevention of intra-abdominal adhesions |
| Colorectal surgery | Colonic anastomosis; rectal fistula repair; treatment of diverticular bleeding; hernia patch placement and hemorrhoidectomy. |
| Liver surgery | Liver resection and liver transplantation. |
| Gynecologic surgery | Hysterectomy; myomectomy for uterine fibroid removal; fallopian tube anastomosis; vaginal fistula repair; cervical surgery; ovarian cyst removal; breast biopsy; mastectomy and lumpectomy and management of preterm premature rupture of membranes. |
| Urologic surgery | Nephrectomy, kidney transplantation; urethral fistula repair; urethral anastomosis; repair for stress urinary incontinence; bladder closure; radical prostatectomy and vasectomy reversal surgery. |
| Pediatric surgery | Congenital cleft lip repair |
| Orthopedic surgery | Hip replacement surgery; knee replacement surgery; tendon reattachment; cartilage repair; intervertebral disc repair, fracture repair and bone grafting |
| Plastic and reconstructive surgery | Face lift surgery; closure of skin incisions; soft tissue augmentation |
| Trauma surgery | Closure of splenic lacerations and other solid organs; closure of skin lacerations; bleeding control during burn debridement and skin grafting for burn victims. |

Polymeric coated gas bubbles acting as ultrasound contrast agents can suitably be embedded in the kits or the medical products described herein before. Polymeric coated gas bubbles derive their contrast properties from the large acoustic impedance mismatch between blood and the gas contained therein. Examples of polymers that can be used to coat these gas bubbles include polylactide, polyglycolide, polycaprolactone, copolymers of polylactide and polyglycolide, copolymers of lactide and lactone, polysaccharide, polyanhydride, polystyrene, polyalkylcyanoacrylate, polyamide, polyphosphazene, poly(methylmethacrylate), polyurethane, copolymers of methacrylic acid and acrylic acid, copolymers of hydroxyethylmethacrylate and methylmethacrylate, polyesters, such as polycarbonates, and protein. Preferred polymers are those which are biocompatible and/or biodegradable. In a preferred embodiment the polymer is polylactic co-glycolic acid (PLGA).

Alternatively, the EL-POX, NU-POX or the cross linked polymer may be produced in such way that gas bubbles are entrapped therein. Preferably, a gas is formed in-situ by reaction of a pH modifier (formulated in the EL-POX phase) with a carbon dioxide releasing base (formulated in the NU-POX phase). Even more preferably, the pH modifier and the carbon dioxide releasing base are formulated in the combined NU-POX/EL-POX phase in which the pH modifier is triggered to lower the pH upon contact with water or bodily fluids The invention is further illustrated by means of the following non-limiting examples.

EXAMPLES

Example 1

Amphiphilic copolymers of EL-POX containing ethyl and NHS groups in the alkyl side chain were synthesized by cationic polymerization of 2-ethyl-2-oxazoline (ETOX) and 2-(3-butenyl)-2-oxazoline (BUTOX) to yield a poly[2-(ethyl/3-butenyl)-2-oxazoline copolymer.

This poly[2-(ethyl/3-butenyl)-2-oxazoline copolymer was functionalized in a two-step approach by first thiol-ene coupling of mercaptopropionic acid followed by activation with NHS to synthesize NHS-side chain activated poly[2-(ethyl/3-butenyl)]-2-oxazoline copolymer. The initial ETOX/BUTOX molar ratio was 90/10 and the percentage of reactive groups per poly[2-(ethyl/3-butenyl)]-2-oxazoline copolymer, was therefore 10%, as explained before.

An amount of 84.3 mg of this NHS-side chain activated poly[2-(ethyl/3-butenyl)]-2-oxazoline copolymer was dissolved in 150 μL ethanol (absolute) and mixed with 150 μL of a mixture of water, ethanol and triethylamine (1:1:1 v/v/v) containing 9.5 mg trilysine triacetate. The combined fluid mixture (about 300 µL containing 28 wt % polymer and a NHS-amine ratio of 1:1.25) turned into a cross linked network (gel) within 30 to 45 seconds.

Example 2

NHS-side chain activated poly[2-(ethyl/3-butenyl)]-2-oxazoline copolymer was synthesized as described in example 1.

An amount of 300 mg of this NHS-side chain activated poly[2-(ethyl/3-butenyl)]-2-oxazoline copolymer was dissolved in 750 µL ethanol (absolute) and 150 µL of trilysine triacetate (10 mg) in ethanol/water 50/50 v/v, containing about 10 µL triethyl amine was added.

The burst pressure of this formulation was tested in the following manner. Briefly, fresh bovine dura was dissected into suitably sized sections of tissue. A 3 mm circular incision was cut into the dura, which was then secured to a burette in such a manner that simulated body fluid could be forced out under measurable pressure via the circular incision.

The formulation containing the active POX copolymer was dried to an amorphous tape by means of vacuum at room temperature and put onto the secured dura to form a seal. After a few minutes, the pressure of the simulated body fluid was increased to the point that the seal burst (burst pressure). The burst pressure was found to be 75 mmHg. The NHS:amine ratio in this film is 2.7:1.

Comparative Example A

The experiment described in Example 2 was repeated (using the same dura), except that this time the film consisted of non-side chain activated poly-ethyl-oxazoline film. This time the burst pressure was found to be about 15 mmHg.

These results show that the incorporation of reactive cross-linking groups in the poly[2-(ethyl/3-butenyl)]-2-oxazoline copolymer, such as NHS, significantly increases the adhesion strength of the tape to the collagen of bovine dura.

Example 3

Amphiphilic copolymers of EL-POX containing ethyl and NHS groups in the alkyl side chain were synthesized by controlled acidic hydrolysis of aquazol 50 (poly(2-ethyl-2-oxazoline (PEtOx), Mw 50,000) to yield a poly[2-ethyl-2-oxazoline/ethylene imine] copolymer (PEtOx-PEI) in which 6% of the initial 2-ethyl-oxazoline units were hydrolyzed.

This poly[2-ethyl-2-oxazoline/ethylene imine] was functionalized in a three-step approach by coupling of methyl succinyl chloride in the presence of triethylamine, followed by the hydrolysis of the methyl ester with lithium hydroxide followed by activation of the obtaining carboxylic acid moieties with NHS in the presence of EDC to synthesize NHS-side chain activated poly(2-ethyl/NHS-ester-ethyl)-2-oxazoline copolymer. The final functionalisation with NHS of the copolymer was determined by UV-vis spectroscopy to be 4.4%.

An amount of 15 mg of this NHS-side chain activated poly[2-(ethyl/NHS-ester-ethyl)]-2-oxazoline copolymer was dissolved in 2174 ethanol (absolute) and mixed with 164 of a mixture of water, ethanol and triethylamine (1:1:1 v/v/v) containing 1.0 mg trilysine. The combined fluid mixture (about 230 µL containing ~6.5 wt % polymer with an NHS-amine ratio of 1.01:1.00) turned into a cross linked network (gel) within 60 seconds at room temperature.

Example 4

NHS-side chain activated poly[2-(ethyl/NHS-ester-ethyl)]-2-oxazoline copolymer was synthesized as described in example 3.

An amount of 410 mg of this NHS-side chain activated poly[2-(ethyl/NHS-ester-ethyl)]-2-oxazoline copolymer was dissolved in 8.25 mL ethanol (absolute) and a solution containing trilysine (5 mg) in 23 µL ethanol, 10 µL water and 10 µL triethyl amine was added. The NHS:amine ratio in this film is 5.5:1.

The burst pressure of this formulation was tested as described in example 2. Instead of fresh bovine dura, bovine peritoneum was used.

The formulation containing the active POX copolymer was dried to an amorphous tape at 40 degrees Celsius and put onto the secured peritoneum to form a seal. After a few minutes, the pressure of the simulated body fluid was increased to the point that the seal burst (burst pressure). The burst pressure was found to be 11 mmHg.

Comparative Example B

An amorphous tape, made in the same way as describe in Example 4, with NHS:amine ratio equals 1:1, was put onto the secured peritoneum to form a seal. After a few minutes, the pressure of simulated body fluid was increased to the point that the seal burst (burst pressure). The burst pressure was found to be 3.7 mm Hg, indicating the importance of having an excess of electrophilic groups to ensure tissue adhesive properties.

Comparative Example C

The 'burst' experiment described in Example 4 was repeated with a film (tape) consisting of non-side chain activated aquazol 50 (poly(2-ethyl-2-oxazoline) (PEtOx), Mw 50,000) film. For this experiment the burst pressure was found to be about 2.6 mmHg. Upon contact with water this film starts to dissolve.

This result shows that incorporation of reactive cross-linking groups in the poly[2-(ethyl/NHS-ester-ethyl)]-2-oxazoline copolymer, such as NHS, significantly increases the adhesion strength of the tape to the collagen of bovine peritoneum.

Example 5

An amorphous tape, made in the same way as described in example 4, but only using the poly[2-(ethyl/NHS-ester-ethyl)]-2-oxazoline copolymer, was put onto the secured peritoneum to form a seal. After a few minutes, the pressure of simulated body fluid was increased to the point that the seal burst (burst pressure). The burst pressure was found to be 3.7 mm Hg. Upon contact with water this film also starts to dissolve.

The adhesion of this tape was excellent. Due to the lack of a nucleophilic cross-linker cohesion was the limiting factor, leading to a moderately low burst pressure (the film was ruptured). Cohesion of this adhesive tape can be improved e.g. by combining the copolymer with a hydrophobic support.

Example 6

NHS-side chain activated poly[2-(ethyl/NHS-ester-ethyl)]-2-oxazoline copolymer was synthesized as described in example 3.

Amine-side chain activated poly[2-(ethyl/NHS-ester-ethyl)]-2-oxazoline copolymer (NU-POX) was synthesized by controlled acidic hydrolysis of aquazol 50 (poly(2-ethyl-2-oxazoline (PEtOx), Mw 50,000) to yield a poly[2-ethyl-2-oxazoline/ethylene imine] copolymer (PEtOx-PEI) in which 12% of the initial 2-ethyl-oxazoline units was hydrolyzed.

This poly[2-ethyl-2-oxazoline/ethylene imine] was functionalized in a two-step approach by first coupling of methyl succinyl chloride in the presence of triethylamine, followed by the reaction of the formed methyl ester side chain with ethylenediamine to yield an amine-side chain activated poly(2-ethyl/amino-ethyl-amide-ethyl)-2-oxazoline copolymer.

A solution containing this NU-POX (3.4 mg) in 2504 borate buffer (0.1 M, pH 8.5) was added to a solution of NHS-side chain activated poly[2-(ethyl/NHS-ester-ethyl)]-2-oxazoline copolymer (10.0 mg) dissolved in 100 μL H$_2$O. The combined fluid mixture (about 350 μL containing ~4 wt % polymer with an NHS-amine ratio of 1.01:1.00) turned into a cross linked network (gel) within 20 seconds at room temperature.

Example 7

NHS-side chain activated poly[2-(ethyl/NHS-ester-ethyl)]-2-oxazoline copolymer was synthesized as described in example 3.

Amine-side chain functionalized poly(2-ethyl/amino-ethyl-amide-ethyl)-2-oxazoline copolymer (NU-POX) was synthesized as described in example 6.

An amount of 266 mg of this NHS-side chain activated poly[2-(ethyl/NHS-ester-ethyl)]-2-oxazoline copolymer was dissolved in 1.33 mL ethanol (absolute) and a solution containing NU-POX (18.4 mg) in 822 μL ethanol (absolute) and 27 μL triethylamine was added. The solution containing the active POX copolymers was dried to an amorphous tape at 40 degrees Celsius and put onto the secured peritoneum to form a seal. The burst pressure of this formulation was determined as described in example 4. The NHS:amine ratio in this film is 5.5:1.

After a few minutes, the pressure of the simulated body fluid was increased to the point that the seal burst (burst pressure). The burst pressure was found to be 23 mmHg, which is significantly higher than the 2.6 mmHg burst pressure of the reference experiment described in Example 5.

These results again show that the incorporation of reactive cross-linking groups in the poly[2-(ethyl/NHS-ester-ethyl)]-2-oxazoline copolymer, such as NHS, significantly increases the adhesive strength of the tape to the collagen of bovine peritoneum. The adhesion of this tape was excellent. Due to the nucleophilic cross linker (NU-POX), the cohesion was good, leading to a relatively high burst pressure. When the burst occurred, the film was not ruptured, meaning that in this case loss of adhesion rather than loss of cohesion was the limiting factor.

Example 8

Amine-side chain functionalized poly(2-ethyl/amino-ethyl-amide-ethyl)-2-oxazoline copolymer was synthesized as described in example 6. This NU-POX was turned into an EL-POX by reacting the amine with maleic anhydride to yield maleimide-side chain activated poly(2-ethyl/maleimide-ethyl-amide-ethyl)-2-oxazoline copolymer.

A thiol derivatized polyethylene glycol (substituted four-arm PEG) polymer was synthesized from an amine derivatized polyethylene glycol (PEG) polymer component consisting of pentaerythritol polyethylene glycol ether tetraamine. The amine groups were coupled to S-acetylthioglycolic acid N-hydroxysuccinimide ester. After removal of the acetyl protecting group of the thiol, the thiol substituted four-arm PEG was obtained.

An amount of 17.5 mg of the maleimide-side chain activated poly[2-(ethyl/maleimide-ethyl-amide-ethyl-2-oxazoline copolymer was dissolved in 100 μL ethanol (absolute) and mixed with 102 μL of a mixture of water and triethylamine (100:2 v/v) containing 32 mg of thiol substituted four-arm PEG thiol. The combined fluid mixture (about 200 μL containing 25 wt % polymer with a maleimide-amine ratio of 3:2) turned into a cross linked network (gel) within 20 seconds at room temperature.

The invention claimed is:

1. A haemostatic powder for producing a biocompatible, tissue-adhesive cross-linked polymer, said haemostatic powder comprising particles containing (i) an electrophilically activated polyoxazoline (EL-POX) and (ii) a nucleophilic cross-linking agent, said EL-POX comprising m electrophilic groups; and said nucleophilic cross-linking agent comprising n nucleophilic groups, having a molecular weight of at least 2,000 g/mol, and being selected from nucleophilically activated POX (NU-POX) comprising at least two amine groups; chitosan; dicarboxy-derivatized chitosan polymers; polyethyleneimines; polyvinylamine; polyallyl amine; amine-functionalized poly(meth)acrylates; amine-functionalized polyethylene glycol; polysaccharides containing amine-functional moieties; polypeptides comprising two or more amino acid residues selected from lysine, ornithine, cysteine, and arginine; and combinations thereof, wherein the EL-POX and the cross-linking agent are not identical;

wherein the m electrophilic groups are capable of reaction with the n nucleophilic groups to form covalent bonds;

wherein m>2, n>2 and m+n>5; and wherein at least one of the m electrophilic groups is a pendant electrophilic group.

2. The haemostatic powder according to claim 1, wherein m exceeds 3.

3. The haemostatic powder according to claim 2, wherein additionally m is at least 13.

4. The haemostatic powder according to claim 1, wherein the EL-POX has a molecular weight of at least 5,000 g/mol.

5. The haemostatic powder according to claim 1, wherein the nucleophilic cross-linking agent has a molecular weight of at least 10,000 g/mol.

6. The haemostatic powder according to claim 1, wherein the electrophilic groups contained in the EL-POX are selected from carboxylic acid esters, sulfonate esters, phosphonate esters, pentafluorophenyl esters, p-nitrophenyl esters, p-nitrothiophenyl esters, acid halide groups, anhydrides, ketones, aldehydes, isocyanato, thioisocyanato, isocyano, epoxides, activated hydroxyl groups, glycidyl ethers, carboxyl, succinimidyl ester, succinimidyl carbonate, succinimidyl carbamates, sulfosuccinimidyl ester, sulfosuccinimidyl carbonate, imido esters, dihydroxyphenylalanine, 3,4-dihydroxyphenylalanine (DOPA), dopamine, 3,4-dihydroxyhydrocinnamic acid (DOHA), norepinephrine, epinephrine, catechol, and combinations thereof.

7. The haemostatic powder according to claim 6, wherein the electrophilic groups present in the EL-POX are selected from aldehydes, succinimidyl esters, succinimidyl carbonates, succinimidyl carbamates, imido esters, dihydroxyphenylalanine, 3,4-dihydroxyphenylalanine (DOPA), dopamine, 3,4-dihydroxyhydrocinnamic acid (DOHA), norepinephrine, epinephrine, catechol, and combinations thereof.

8. The haemostatic powder according to claim 7, wherein the electrophilic groups present in the EL-POX are selected from N-hydroxysuccinimide esters, aldehydes, dihydroxyphenylalanine, 3,4-dihydroxyphenylalanine (DOPA), dopamine, 3,4-dihydroxyhydrocinnamic acid (DOHA), norepinephrine, epinephrine, catechol, and combinations thereof.

9. The haemostatic powder according to claim 1, wherein the ratio m:n is at least 1:1.

10. The haemostatic powder according to claim 1, wherein the EL-POX comprises an excess amount of electrophilic groups relative to the amount of nucleophilic groups contained in the nucleophilic cross-linking agent.

11. The haemostatic powder according to claim 1, wherein the powder comprises EL-POX and the nucleophilic cross-linking agent in a molar ratio of at least 1:1.

12. The haemostatic powder according to claim 1, wherein 3-50% of the side chains of the EL-POX contain an electrophilic group.

13. The haemostatic powder according to claim 1, wherein the powder contains 25-75 wt. % of the EL-POX, 25-75 wt. % of the nucleophilic cross-linking agent and 0-50 wt. % of carrier selected from monosaccharides; di- and oligosaccharides; polysaccharides; and combinations thereof.

\* \* \* \* \*